United States Patent [19]

Chodorge et al.

[11] Patent Number: 4,966,995
[45] Date of Patent: Oct. 30, 1990

[54] PROCESS FOR THE PREPARATION OF CHLORIDES OF CARBOXYLIC ACIDS

[75] Inventors: Jeannine Chodorge, Antony; Jean-Pierre Senet, Herbeauvilliers-Buthiers; Gary Wooden, Mennecy, all of France

[73] Assignee: Societe Nationale Des Poudres et Explosifs, Paris, France

[21] Appl. No.: 258,634

[22] Filed: Oct. 17, 1988

[30] Foreign Application Priority Data

Nov. 5, 1987 [FR] France ................. 87 15344

[51] Int. Cl.$^5$ ............................................ C07C 51/58
[52] U.S. Cl. ................................................... 562/861
[58] Field of Search ......................................... 562/861

[56] References Cited

FOREIGN PATENT DOCUMENTS

| 758209 | 4/1971 | Belgium . |
| 2704192 | 8/1978 | Fed. Rep. of Germany . |
| 1548509 | 12/1968 | France . |
| 1556386 | 2/1969 | France . |
| 7082336 | 5/1982 | Japan . |
| 1219953 | 1/1971 | United Kingdom . |

*Primary Examiner*—Paul J. Killos
*Attorney, Agent, or Firm*—Bucknam and Archer

[57] ABSTRACT

The invention relates to a new process for the preparation of chlorides of carboxylic acids by reaction of tetrachloroethylene carbonate with a carboxylic acid of formula $R(COOH)_n$ at a temperature of between 80° and 160° C.

The radical R may be very diverse and n is an integer which can take the values 1 to 4.

A solvent is not necessary. A catalyst may be employed.

Acyl chlorides of a high purity are obtained.

10 Claims, No Drawings

PROCESS FOR THE PREPARATION OF CHLORIDES OF CARBOXYLIC ACIDS

The invention relates to a new process for the preparation of chlorides of caboxylic acids from the corresponding caboxylic acids.

Various processes for the preparation of chlorides of carboxylic acids from carboxylic acids have been proposed (cf "Methoden der Organischen Chemie" Houben-Weyl, Vol 8, pp. 464 et seq.).

Thus, it is possible to employ phosphorus pentachloride

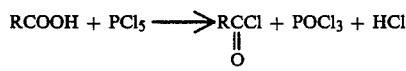

but this is a product which is solid and sensitive to hydrolysis, and consequently not very convenient in use, -phosphorus trichloride,

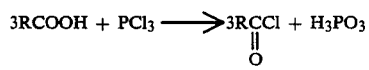

a large excess of the order of 25 to 100% is needed and the yields are highly variable because of numerous secondary reactions ("The Chemistry of Acyl halides" Saul Pataï, Intersciences Publishers - Wiley & Sons (1972) p. 41). - thionyl chloride,

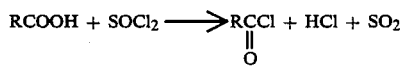

the addition of a catalyst is generally necessary (H.M. Bosshard et al., Helv. Chem. Acta (1959) 62 1633) - cxalyl chloride

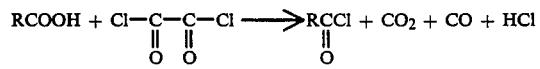

its toxicity is high and it is an expensive product (N.O.V. Sonntag et al., J. Am. Oil Chemist Soc. (1954) 31, 151) - phosgene

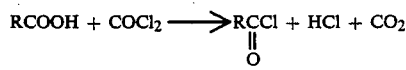

but in the absence of catalyst the reaction must be carried out at high temperature and at high pressure (U.S. Pat. No. 2,657,233). Moreover, it is a toxic product, which requires highly specific plants situated near its production site because its transport is dangerous.

It is found that the use of the various processes according to the prior art always presents disadvantages. Either the acyl chlorides are obtained with interfering byproducts or else the reaction is difficult to perform because of toxicity problems.

It was consequently very important to have access to a new process for the preparation of chlorides of carboxylic acids, in which less dangerous products were employed ad which made it possible to obtain acyl chlorides of high purity.

The present invention fulfils this expectation and its subject is a process for the preparation of acyl chlorides with a reactant which is not highly toxic and which does not give rise to impurities.

The process according to the invention is a process for the preparation of chlorides of carboxylic acids by reaction of tetrachloroethylene carbonate with the corresponding carboxylic acids, at a temperature of between 80° C. and 160° C. The reaction scheme is the following:

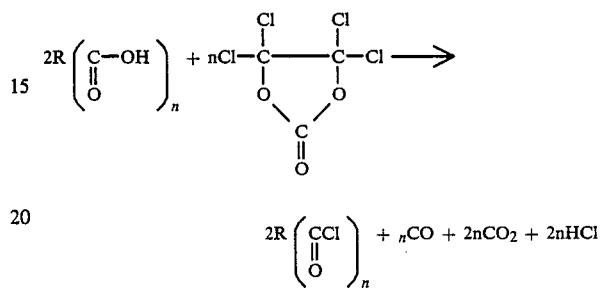

Tetrachloroethylene carbonate which is used to implement the process according to the invention is a known compound. It can be easily prepared by a photochemical reaction of chlorine with ethylene carbonate, as described in U.S. Pat. No. 2,816,287:

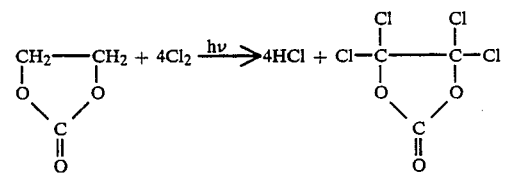

The carboxylic acids with which it is used to react are very numerous and diverse. They are to be found commercially or are prepared according to known methods.

The addition of a catalyst is not necessary.

The use of a solvet will be possible when this is really indispensable as, for example, when the acyl halides have a low boiling point or when the acids have a high melting point.

The acyl chlorides obtained are consequently very pure, free from interfering products.

The implementation of the process is simple. A distilation is not indispensable for recovering the acyl chlorides, and this advantage is particularly valuable in the preparation of acyl chlorides which are unstable or which have a high boiling point.

The invention is described in detail hereinafter.

The process according to the invention is applicable in particular to the carboxylic acids of formula R(COOH)$_n$, in which R denotes a linear or branched C$_1$–C$_{30}$ alkyl radical which may contain one or more double or triple carbon-carbon bonds and one or more substituents chosen from halogen atoms and aryl, aryloxy, alkoxy, alkyloxycarbonyl, aryloxycarbonyl and 5- or 6-membered heterocyclic radicals, saturated or unsaturated, the hetero atom(s) being chosen from sulphur or oxygen atoms, a C$_3$–C$_7$ cycloalkyl radical which may contain one or more carbon-carbon double bonds when it contains from 5 to 7 carbon atoms, and which may carry one or more substituents chosen from halogen atoms and alkyl, alkenyl, aryl, alkyloxycarbonyl and aryloxycarbonyl radicals, a condensed or otherwise aromatic or heteroaromatic radical, the hetero atom(s) being chosen from sulphur, oxygen or nitrogen atoms, which may carry one or more substituents chosen from halogen atoms, alkyl or haloalkyl radicals comprising or not comprising one or more double or triple bonds, aryl, alkoxy, aryloxy, alkyloxycarbonyl and aryloxycarbonyl radicals and nitro and cyano groups, a 5- or 6-membered nonaromatic heterocyclic radical comprising one or more hetero atoms chosen from oxygen and sulphur, capable of comprising one or more double bonds and substituted or otherwise by one or more alkyl, alkyloxycarbonyl and aryloxycarbonyl radicals, and n denotes an integer which can take the values 1 to 4.

More particularly, the radical R denotes a linear or branched $C_1$-$C_{20}$ alkyl radical which may contain one or more double or triple carbon-carbon bonds and one or more substituents chosen from chlorine, bromine or fluorine atoms and $C_1$-$C_4$ alkoxy, phenyl, naphthyl, phenoxy, naphthoxy, $C_1$-$C_4$ alkyloxycarbonyl, phenoxycarbonyl, furyl, pyranyl and thienyl radicals, a $C_3$-$C_6$ cycloalkyl radical which may comprise a double bond when it contains from 5 to 6 carbon atoms and which may carry one or more substituents chosen from $C_1$-$C_5$ alkyl and alkenyl radicals, an aromatic or heteroaromatic radical, the hetero atom(s) being chosen from sulphur, oxygen or nitrogen atoms, comprising 5- or 6-membered heterocyclic rings, condensed or otherwise, and which may carry one or more substituents chosen from halogen atoms, $C_1$-$C_{12}$ alkyl, fluoro- or chloroalkyl radicals comprising or not comprising one or more double or triple bonds, $C_6$-$C_{10}$ aryl, $C_1$-$C_{12}$ alkoxy, $C_6$-$C_{10}$ aryloxy, $C_1$-$C_4$ alkyloxycarbonyl and phenoxycarbonyl radicals, and nitro and cyano groups, in particular the phenyl, naphthyl, furyl, benzofuryl, phenoxy and naphthoxy radical, and n denotes the value 1 or 2.

As an example of acids which may be employed within the scope of the invention, there may be mentioned propionic, butyric, isobutyric, valeric, isovaleric, pivalic, hexanoic, octanoic, decanoic, lauric, palmitic, stearic, tricontanoic, undecylenic, acrylic, methacrylic, crotonic, isocrotonic, propargylic, vinylacetic, oleic, chloroacetic, dichloroacetic, trichloroacetic, bromoacetic, dibromoacetic, tribromoacetic, alpha-chloropropionic, alpha-chlorobutyric, malonic, succinic, adipic and sebacic acid, the monomethyl ester of malonic acid, the monomethyl ester of succinic acid, phenylacetic, phenyloxyacetic,beta-phenylpropionic,beta-phenyloxypropionic, cyclopropanecarboxylic, 2,2-dimethyl-3-(2-methylpropenyl)cyclopropanecarboxylic,cyclohexanecarboxylic,1,4-cyclohexanedicarboxylic, cyclohexenecarboxylic, 2-thienyl-4-butyric, methoxyacetic, tiglic, angelic, fumaric, maleic, brassylic, benzoic and toluic acid, halobenzoic acids, mononitrobenzoic acids, cyanobenzoic acids, isophthalic, terephthalic, 3-phenoxybenzoic, 4-tertbutylbenzoic, furoic, benzofuroic, thenoic, nicotinic, isonicotinic and quinolinecarboxylic acid, indolecarboxylic acids, biphenylcarboxylic, 3,4,5-methoxybenzoic and 4-methoxycarbonylbenzoic acid, trifluoromethylbenzoic acids and naphthalenecarboxylic acids.

Tetrachloroethylene carbonate is preferably added progressively to the reaction medium which has been heated and kept at the chosen temperature. It is generally employed in a quantity of between 0.50 and 0.75 equivalent per equivalent of acidic group to be converted, preferably between 0.52 and 0.6 equivalent.

Wherever possible it is preferable to perform the reaction without any solvent. When it is desired to prepare acyl chlorides of low boiling point or whose corresponding acids have a high melting point, for example above 140° C., it is possible to employ one or more inert solvents chosen, for example, from chlorinated aliphatic solvents such as 1,2-dichloroethane, or aromatic solvents such as toluene, xylene, chlorobenzene and dichlorobenzenes.

Although a catalyst is not absolutely necessary in order to perform the reaction, the addition of catalytic compounds may make it possible to shorten the reaction times and/or to lower the temperature.

The catalysts are chosen from the catalysts which are already known and employed in the reactions for preparing chlorides of carboxylic acids, described earlier.

In particular, they are chosen from the group which comprises:

tertiary amines and their hydrochlorides, in particular pyridine and 4-N,N-dimethylpyridine (DMAP), quaternary ammonium salts and in particular chlorides and bromides, for example those of tetra-n-butyl and those of benzyltri-n-butyl, quaternary phosphonium salts, N,N-disubstituted amides, in particular N,N-dimethylformamide and their reaction products with compounds such as $PCl_3$, $PCl_5$, $POCl_3$, $COCl_2$, $SOCl_2$ and $(CO)_2Cl_2$ (Vilsmeier-Haack salts), tetrasubstituted ureas, in particular tetramethylurea and tetrabutylurea, and their reaction products with the compound agents such as $PCl_3$, $PCl_5$, $POCl_3$, $COCl_2$, $SOCl_2$ and $(CO)_2Cl_2$, hexaalkylphosphoramides such as hexamethylphosphorotriamide (HMPT), hexaalkylguanidinium salts, in particular chlorides, and their hydrochlorides, as described in Patent Application EP No. 213,976, in particular hexamethyl- and hexabutylguanidinium chlorides.

The quantity of catalyst which is added is generally between $10^{-4}$ and $10^{-1}$ equivalent per equivalent of acidic group to be converted. The chlorination temperature is between 80° and 160° C. In the absence of a catalyst the reaction is generally performed at a temperature of between 110° and 160° C., preferably between 120° C. and 160° C. When a catalyst is employed, the reaction is generally performed between 80° and 150° C. and preferably between 100° and 135° C.

The reaction time is generally between 1 and 4 hours.

Acyl chlorides of a high purity, which it will be possible to employ without subsequent purification, are obtained, by virtue of the process of the invention, in a simple manner, from relatively inexpensive and non-toxic starting materials.

Acyl chlorides are well-known compounds whose applications are numerous. They are employed, for example, as synthesis intermediates for the preparation of esters, amides, peresters and peroxides, polymeric compounds, pesticidal and pharmaceutical products and in the papermaking industry.

The examples which follow illustrate the invention without, however, limiting it.

EXAMPLES 1 to 11

General operating procedure

The carboxylic acid, the solvent where appropriate, and the catalyst are introduced into a reactor equipped with a stirrer, a thermometer and a reflux condenser. The reaction mixture is heated to the temperature indicated and 0.50 to 0.6 equivalent of tetrachloroethylene carbonate (TCEC) per acidic group to be converted is introduced slowly while the temperature is maintained. At the end of the reaction (followed using IR or VPC), the acyl chloride is separated by distillation from the residual tetrachloroethylene carbonate, if necessary.

The operating conditions and the results are collated in the following table

We claim:
1. Process for the preparation of chlorides of carboxylic acids, characterized in that tetrachloroethylene carbonate is reacted with a carboxylic acid at a temperature of between 80° C. and 160° C.
2. Process according to claim 1, characterized in that tetrachloroethylene carbonate is added progressively to the preheated reaction medium.
3. Process according to claim 1 or 2, characterized in that tetrachloroethylene carbonate is added in a quantity of between 0.50 and 0.75 equivalent per equivalent of acidic group to be converted, preferably between 0.52 and 0.6 equivalent.

TABLE 1

| Ex. | Acid | TCEC Qty. | Catalyst | Solvent | T(°C.)/Time | Yield (Distilled) |
|---|---|---|---|---|---|---|
| 1 | Et-Bu—CHCO$_2$H  144 g (1.00 mole) | 135.6 g  0.60 mole | (Bu$_2$N)$_3$⊕CCl⊖  0.086 g (0.0002 mole) | none | 120–135°/3 h | 94% |
| 2 | furan-CO$_2$H  33.6 g (0.30 mole) | 37.3 g  0.17 mole | Me$_2$N—C$_5$H$_4$N  0.16 g (0.0013 mole) | PhCH$_3$  41 ml | 105°/1 h | 90% |
| 3 | PhCO$_2$H  36.6 g (0.30 mole) | 40.7 g  0.18 mole | (Bu$_2$N)$_2$—C=O  0.43 g (0.0015 mole) | none | 130–135°/1 h | 98% |
| 4 | CH$_3$(CH$_2$)$_{16}$CO$_2$H  0.20 mole | 0.11 mole | (Bu$_2$N)$_3$C⊕HCl$_2$⊖  (0.00004 mole) | none | 105°/1 h | quantitative (not distilled) |
| 5 | Et-BuCHCO$_2$H  0.10 mole | 0.06 mole | none | none | 130–140°/2 h | 86% |
| 6 | cyclopropyl-CO$_2$H  1.00 mole | 0.55 mole | none | none | 150°/3 h | 83% |
| 7 | CH$_2$=CH(CH$_2$)$_8$CO$_2$H  0.50 mole | 0.28 mole | none | none | 150°/2 h | 86% |
| 8 | HO$_2$C(CH$_2$)$_4$CO$_2$H  1.00 mole | 1.05 mole | none | none | 105°/3 h | 60% |
| 9 | 2-CF$_3$-C$_6$H$_4$-CO$_2$H  0.10 mole | 0.055 mole | none | none | 120°/1 h | 91% |

| Ex. | Acid | TCEC Qty. | Catalyst | Solvent | T(°C.)/Time | Yield* |
|---|---|---|---|---|---|---|
| 10 | (C$_6$H$_5$)-O-(C$_6$H$_4$)-COOH  64.2 g (0.3 mole) | 35.9 g  0.159 mole | none | PhCl  150 g | 120–132°/12 h | 62% |
| 11 | NO$_2$-C$_6$H$_4$-COOH  50.1 g (0.3 mole) | 35.9 g  0.159 mole | none | O-di chloro benzene  50 g | 140–160°/10 h | 77% |

*Yield calculated from acid chlorid content

4. Process according to claim 1, characterized in that the carboxylic acid has the formula $R(COOH)_n$, in which R denotes

- a linear or branched $C_1$–$C_{30}$ alkyl radical which may contain one or more double or triple carboncarbon bond and one or more substituents chosen from halogen atoms and aryl, aryloxy, alkoxy, alkyloxycarbonyl, aryloxycarbonyl and 5- or 6-membered heterocyclic radicals, saturated or unsaturated, the hetero atoms being chosen from sulphur or oxygen atoms,
- a $C_3$–$C_7$ cycloalkyl radical which may contain one or more carbon-carbon double bonds when it contains from 5 to 7 carbon atoms, and which may carry one or more substituents chosen from halogen atoms and alkyl, alkenyl, aryl, alkyloxycarbonyl and aryloxycarbonyl radicals,
- a condensed or otherwise aromatic or hetero aromatic radical, the hetero atom(s) being chosen from sulphur, oxygen or nitrogen atoms, which may carry one or more substituents chosen from halogen atoms, alkyl or haloalkyl radicals comprising or not comprising one or more double or triple bonds, aryl, alkoxy, aryloxy, alkyloxycarbonyl and aryloxycarbonyl radicals and nitro and cyano groups,
- a 5- or 6-membered nonaromatic heterocyclic radical, comprising one or more hetero atoms chosen from oxygen or sulphur, capable of comprising one or more double bonds and substituted or otherwise by one or more alkyl, alkyloxycarbonyl and aryloxycarbonyl radicals, and n denotes an integer which can take the values of 1 to 4.

5. Process according to claim 4, characterized in that the radical R denotes

- a linear or branched $C_1$–$C_{20}$ alkyl radical which may contain one or more double or triple carboncarbon bonds and one or more substituents chosen from chlorine, bromine or fluorine atoms and $C_1$–$C_4$ alkoxy, phenyl, naphthyl, phenoxy, naphthoxy, $C_1$–$C_4$ alkyloxycarbonyl, phenoxycarbonyl, furyl, pyranyl and thienyl radicals,
- a $C_3$–$C_6$ cycloalkyl radical which may comprise a double bond when it contains from 5 to 6 carbon atoms and which may carry one or more substituents chosen from $C_1$–$C_5$ alkyl and alkenyl radicals,
- an aromatic or heteroaromatic radical, the hetero atom(s) being chosen from sulphur, oxygen or nitrogen atoms, comprising 5- or 6-membered heterocyclic rings, condensed or otherwise, and which may carry one or more substituents chosen from halogen atoms, $C_1$–$C_{12}$ alkyl, fluoro- or chloroalkyl radicals comprising or not comprising one or more double or triple bonds, $C_6$–$C_{10}$ aryl, $C_1$–$C_{12}$ alkoxy, $C_6$–$C_{10}$ aryloxy, $C_1$–$C_4$ alkyloxycarbonyl and phenoxycarbonyl radicals, and nitro and cyano groups, and n denotes the value 1 or 2.

6. Process according to claim 1, characterized in that one or more solvents chosen from chlorinated aliphatic solvents and aromatic solvents are employed.

7. Process according to claim 1, characterized in that a catalyst is employed, chosen from the group which comprises:
- tertiary amines and their hydrochlorides,
- quaternary ammonium salts,
- quaternary phosphonium salts,
- N,N-disubstituted amides and their reaction products with $PCl_3$, $PCl_5$, $POCl_3$, $COCl_2$, $SOCl_2$ or $(CO)_2Cl_2$,
- tetrasubstituted ureas and their reaction products with $PCl_3$, $PCl_5$, $POCl_3$, $COCl_2$, $SOCl_2$ or $(CO)_2Cl_2$,
- hexaalkylphosphoramides,
- hexaalkylguanidinium salts and their hydrochlorides 8. Process according to claim 1, characterized in that the catalyst is employed in a quantity of between $10^{-4}$ and $10^{-1}$ equivalent per equivalent of acidic group to be converted.

9. Process according to claim 1, characterized in that the temperature is between 110° and 160° C. in the absence of catalyst and between 80° and 150° C. when a catalyst is employed.

10. Process according to claim 1, characterized in that the temperature is between 120° and 160° C. in the absence of catalyst and between 100° and 135° C. when a catalyst is employed.

* * * * *